United States Patent
Wolford

(10) Patent No.: US 6,951,563 B2
(45) Date of Patent: Oct. 4, 2005

(54) ORTHOPAEDIC REAMER WITH FLAT CUTTING TEETH

(75) Inventor: Todd Wolford, Goshen, IN (US)

(73) Assignee: Symmetry Medical, Inc., Warsaw, IN (US)

( * ) Notice: Subject to any disclaimer, the term of this patent is extended or adjusted under 35 U.S.C. 154(b) by 113 days.

(21) Appl. No.: 10/104,738

(22) Filed: Mar. 22, 2002

(65) Prior Publication Data

US 2003/0181916 A1 Sep. 25, 2003

(51) Int. Cl.$^7$ .............................................. A61B 17/00
(52) U.S. Cl. ....................................................... 606/81
(58) Field of Search ........................... 606/81, 80, 79, 606/82, 86, 90, 91; 623/22.21, 22.31, 22.39, 22.32; 408/14; 407/54, 61

(56) References Cited

U.S. PATENT DOCUMENTS

| | | | | |
|---|---|---|---|---|
| 4,023,572 A | * | 5/1977 | Weigand et al. ............... | 606/81 |
| 5,462,548 A | * | 10/1995 | Pappas et al. ................. | 606/80 |
| 5,709,688 A | * | 1/1998 | Salyer .......................... | 606/81 |
| 5,976,144 A | * | 11/1999 | Fishbein et al. ............... | 606/80 |
| 6,001,105 A | * | 12/1999 | Salyer .......................... | 606/81 |
| 6,168,600 B1 | * | 1/2001 | Grace et al. ................... | 606/81 |
| 6,428,543 B1 | * | 8/2002 | Salyer .......................... | 606/81 |
| 6,475,221 B1 | * | 11/2002 | White et al. ................... | 606/80 |

* cited by examiner

*Primary Examiner*—Pedro Philogene
(74) *Attorney, Agent, or Firm*—Taylor & Aust, P.C.

(57) ABSTRACT

An orthopaedic reamer for cutting bone includes a shaft and a head coupled with the shaft. The head includes a distal face with a plurality of cutting teeth. Each cutting tooth includes a hole extending through the head. At least a portion of each hole has a substantially round perimeter. A raised lip is positioned adjacent to and extends around at least part of the substantially round portion.

22 Claims, 1 Drawing Sheet

ORTHOPAEDIC REAMER WITH FLAT CUTTING TEETH

BACKGROUND OF THE INVENTION

1. Field of the Invention

The present invention relates to orthopeadic reamers, and, more particularly, to orthopeadic reamers having a distal cutting face.

2. Description of the Related Art

An orthopeadic reamer is used to cut a bone and thereby form the bone with a predetermined shape for receiving an orthopeadic implant. For example, an intramedullary reamer may be placed into the intramedullary canal of the bone and used to ream the interior of the bone to receive the stem of an orthopeadic implant. Such a reamer includes a radial, peripheral surface which generally includes a plurality of radially extending teeth for cutting the bone in a radial direction as the reamer proceeds in an axial direction into the bone. The size of the opening formed in the bone is determined by the outside diameter of the reamer.

An orthopeadic reamer may also include a cutting head with a distal face which has a plurality of cutting teeth formed therein. The distal face has a shape which corresponds to the shape of an orthopeadic implant to be received within the bone, and includes a plurality of cutting teeth extending from the distal face. The reamer is placed against the bone surface to be cut, such as an acetabulum or glenoid, and is plunge cut into the bone. Such reamers are effective for removing a portion of the bone so that the bone is shaped to receive the implant.

An orthopeadic reamer including a distal face as described above may include cutting teeth which are formed by a punching operation for each individual tooth. Each cutting tooth typically includes a hole and a raised portion which extends from the distal face. The raised portion includes a humped or center portion which results in the bone being cut with an annular groove as the cutting head is rotated about its rotational axis. In other words, each cutting tooth includes a raised portion resembling half of a cone split longitudinally, with the base edge of the cone defining the cutting edge. Although such a cutting tooth configuration is effective to remove the bone for receiving an implant, the rough surface resulting from the cutting teeth may not be desirable for certain applications.

What is needed in the art is an orthopeadic reamer used for plunge cuts which effectively yet smoothly removes the bone.

SUMMARY OF THE INVENTION

The present invention provides an orthopeadic reamer including a cutting head with a plurality cutting teeth, with each cutting tooth having a raised lip adjacent a round portion of a hole.

The invention comprises, in one form thereof, an orthopaedic reamer for cutting bone including a shaft and a head coupled with the shaft. The head includes a distal face with a plurality of cutting teeth. Each cutting tooth includes a hole extending through the head. At least a portion of each hole has a substantially round perimeter. A raised lip is positioned adjacent to and extends around at least part of the substantially round portion.

An advantage of the present invention is that the configuration of the cutting teeth allows them to be formed using a simple stamping operation.

Another advantage is that the cutting teeth are configured to cut the bone fast and smoothly.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
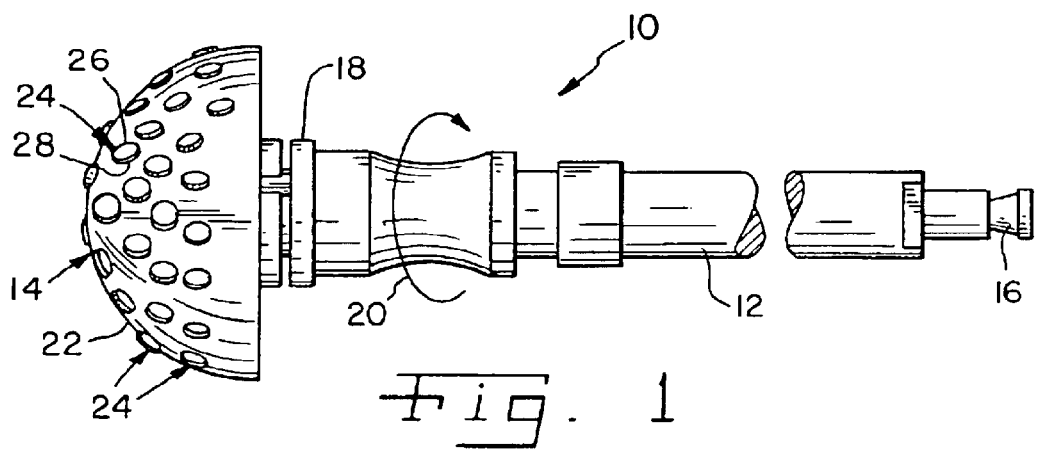
FIG. 1 is a side view of an embodiment of an orthopeadic reamer of the present invention.

Referring now to the drawings, there is shown an embodiment of an orthopeadic reamer 10 of the present invention which is used for cutting bone. In the embodiment shown, orthopeadic reamer 10 is an acetabular reamer used to cut an acetabulum, but may also be configured to cut bone such as a shoulder or knee joint. Orthopeadic reamer 10 generally includes a shaft 12 and a head 14.

Shaft 12 includes a driven end 16 and a distal end 18. Driven end 16 is removably coupled with a source of rotational power for rotatably driving shaft 12 in a driven direction, as indicated by arrow 20. Distal end 18 is coupled with head 14 in any suitable manner, such as welding, threaded engagement, twist and lock, bayonet fittings, etc.

Head 14 includes a distal face 22 which is placed against a bone to be cut, and includes a predetermined shape which is dependent upon a particular application. In the embodiment shown, distal face 22 has a generally hemispherical shape with a predetermined radius of curvature for cutting an acetabulum associated with a hip joint.

Head 14 also includes a plurality of cutting teeth 24 which are formed in distal face 22 by a punching operation. Cutting teeth 24, shown more particularly in FIGS. 2 and 3, have a common shape with a leading edge 26 and a trailing edge 28 relative to driven direction 20. It is possible to form a head 14 having cutting teeth 24 with different shapes on the same head and still stay within the scope of this invention. However, this is probably not likely because of additional costs associated with using different punching tools to form cutting teeth 24 in cutting head 14.

Figure 2:
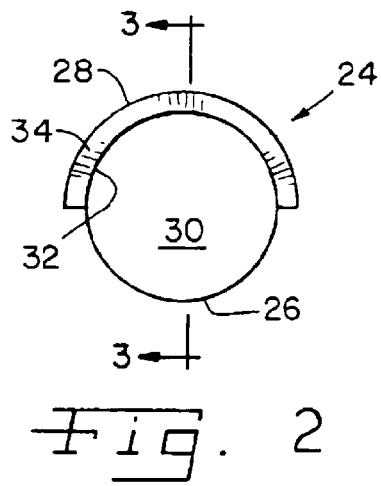
FIG. 2 is a plan view of one of the cutting teeth on the cutting head of the orthopeadic reamer of FIG. 1.
Figure 3:
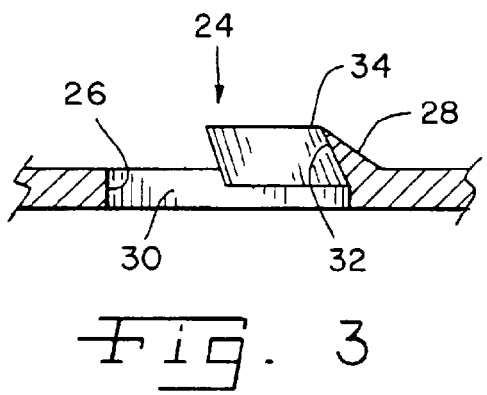
FIG. 3 is a sectional view of the cutting tooth of FIG. 2, taken along line 3—3.

Referring now to FIGS. 2 and 3, a cutting tooth 24 of cutting head 14 shown in FIG. 1 will be described in more detail. Each cutting tooth 24 is formed using a multiple punch operation. Each cutting tooth 24 includes a hole 30 extending through cutting head 14. Hole 30 is formed with at least a portion thereof having a substantially round perimeter 32. A raised lip 34 is concentrically positioned adjacent to and extends around at least a part of the substantially round perimeter 32 of hole 30. In the embodiment shown in FIGS. 2 and 3, hole 30 is a round hole and raised lip 34 extends approximately halfway around hole 30. Raised lip 34 is positioned adjacent trailing edge 28, relative to driven direction 20.

By forming cutting tooth 24 with raised lip 34 as shown and described above, raised lip 34 has a generally flat cutting surface for cutting the bone. Thus, in contrast with previously known cutting shapes having a curved or humped cutting lip, cutting tooth 24 of the present invention provides a raised lip 34 with a generally flat upper surface which results in a smooth cut of the bone.

Figure 4:
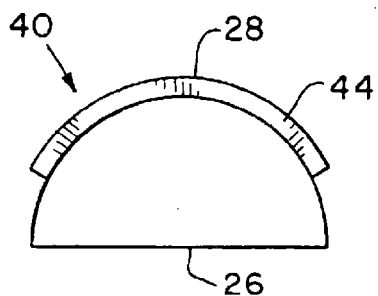
FIG. 4 is a plan view of another embodiment of a cutting tooth of the present invention for use with an orthopeadic reamer.
Figure 5:
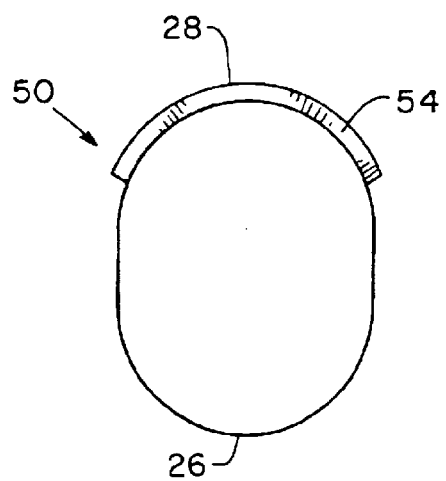
FIG. 5 is a plan view of yet another embodiment of a cutting tooth of the present invention for use with an orthopeadic reamer.

FIGS. 4 and 5 illustrate alternative embodiments of a cutting tooth 40 and 50, respectively, of the present invention for cutting bone. In each example, cutting tooth 40 and 50 includes a hole 42 and 52, respectively, with a portion thereof having a substantially round perimeter. A raised lip 44 and 54, respectively, is positioned adjacent to the round portion of the hole 42, 52 at trailing edge 28. The extent to which raised lips 44 and 54 extend around the round portion of holes 42, 52 may vary, depending upon the particular application. Cutting teeth with differently shaped holes are also possible, as long as the cutting tooth includes a hole with at least a portion thereof having a round perimeter so that the raised lip may be formed concentrically thereabout using a punching operation.

During manufacture, cutting teeth 24, 40 or 50 are formed in cutting head 14 using a punching operation. For each cutting tooth, a hole is first punched or established using other appropriate processes such as laser cutting, etc. into cutting head 14 including at least a portion thereof with a substantially round perimeter. A raised lip 34, 44 or 54 is then formed adjacent the substantially round perimeter of the hole, such that the raised lip lies generally concentric with the round portion of the hole. Placing the raised lip adjacent the round perimeter of the hole allows the raised lip to be evenly raised therearound so that the distal cutting edge of the raised lip is generally flat. In this manner, the bone may be cut smoothly.

During an orthopeadic operation, head 14 of orthopeadic reamer 10 is placed against a bone (not shown) to be cut. Orthopeadic reamer 10 is then driven in driven direction 20 using a rotating driver (not shown). As orthopeadic reamer 10 rotates, cutting teeth 24 cut the bone using the plurality of cutting teeth 24. When the bone is properly prepared for an implant, orthopeadic reamer 10 is removed.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic reamer for cutting bone, comprising:
   a shaft; and
   a cutting head coupled with said shaft, said cutting head including a distal face with a plurality of cutting teeth, each said cutting tooth including a hole extending through said head, at least a portion of said hole having a substantially round perimeter, and a raised lip adjacent to and extending around at least part of said substantially round portion, said raised lip generally concentric to said substantially round perimeter, said raised lip substantially evenly raised around said at least part of said substantially round portion, said raised lip both extending from said cutting head and monolithic with said cutting head.

2. The orthopaedic reamer of claim 1, wherein each said cutting tooth has a hole which is one of round, oval and D-shaped.

3. The orthopaedic reamer of claim 2, wherein said cutting head is rotatable in a driven direction, and each said cutting tooth has a hole with a leading edge and a trailing edge relative to said driven direction, said raised lip positioned adjacent said trailing edge.

4. The orthopaedic reamer of claim 3, wherein each said cutting tooth has a hole which is round, and said raised lip is positioned adjacent said trailing edge.

5. The orthopaedic reamer of claim 4, wherein said raised lip extends approximately halfway around said hole.

6. The orthopaedic reamer of claim 3, wherein each said cutting tooth has a hole which is oval with a substantially round portion adjacent said trailing edge, and said raised lip is positioned adjacent said trailing edge.

7. The orthopaedic reamer of claim 3, wherein each said cutting tooth has a hole which is D-shaped with a substantially round porton adjacent said trailing edge, and said raised lip is positioned adjacent said trailing edge.

8. The orthopaedic reamer of claim 2, wherein said cutting teeth have corresponding holes with a common shape.

9. The orthopaedic reamer of claim 1, wherein said cutting head is rotatable in a driven direction, and each said cutting tooth has a hole with a leading edge and a trailing edge relative to said driven direction, said raised lip positioned adjacent said trailing edge.

10. The orthopaedic reamer of claim 1, wherein each said cutting tooth is formed using a punching operation.

11. The orthopaedic reamer of claim 1, wherein said distal face is generally hemispherical shaped.

12. A cutting head for an orthopaedic reamer, comprising a distal face with a plurality of cutting teeth, each said cutting tooth including a hole extending through said head, at least a portion of said hole having a substantially round perimeter, and a raised lip adjacent to and extending around at least part of said substantially round portion, said raised lip generally concentric to said substantially round perimeter, said raised lip substantially evenly raised around said at least part of said substantially round portion, said raised lip both extending from said cutting head and monolithic with said cutting head.

13. The cutting head of claim 12, wherein each said cutting tooth has a hole which is one of round, oval and D-shaped.

14. The cutting head of claim 13, wherein said head is rotatable in a driven direction, and each said cutting tooth has a hole with a leading edge and a trailing edge relative to said driven direction, said raised lip positioned adjacent said trailing edge.

15. The cutting head of claim 14, wherein each said cutting tooth has a hole which is round, and said raised lip is positioned adjacent said trailing edge.

16. The cutting head of claim 15, wherein said raised lip extends approximately half way around said hole.

17. The cutting head of claim 14, wherein each said cutting tooth has a hole which is oval with a substantially round porton adjacent said trailing edge, and said raised lip is positioned adjacent said trailing edge.

18. The cutting head of claim 14, wherein each said cutting tooth has a hole which is D-shaped with a substantially round porton adjacent said trailing edge, and said raised lip is positioned adjacent said trailing edge.

19. A method of manufacturing an orthopaedic reamer, comprising the steps of:

forming a cutting head including a distal face; and forming a plurality of cutting teeth through said cutting bead and extending from said distal face, each said cutting tooth including a hole extending through said head, at least a portion of said hole having a substantially round perimeter, and a raised lip adjacent to and extending around at least part of said substantially round portion, said raised lip generally concentric to said substantially round perimeter, said raised lip substantially evenly raised around said at least part of said substantially round portion, said raised lip both extending from said cutting head and monolithic with said cutting head.

20. The orthopaedic reamer of claim 1, wherein said raised lip includes a cross-section which is substantially a parallelogram.

21. The cutting head of claim 12, wherein said raised lip includes a cross-section which is substantially a parallelogram.

22. The method of claim 19, wherein said raised lip includes a cross-section which is substantially a parallelogram.

* * * * *